United States Patent [19]

Prockop et al.

[11] Patent Number: 5,861,502
[45] Date of Patent: Jan. 19, 1999

[54] ANTISENSE OLIGONUCLEOTIDES TO INHIBIT EXPRESSION OF MUTATED AND WILD TYPE GENES FOR COLLAGEN

[75] Inventors: Darwin Prockop, Philadelphia, Pa.; Alain Colige, Sart Tilman Par Liege, Belgium; Renato Baserga, Ardmore; Paul Nugent, Philadelphia, both of Pa.

[73] Assignee: Thomas Jefferson University, Philadelphia, Pa.

[21] Appl. No.: 432,158

[22] PCT Filed: Nov. 9, 1993

[86] PCT No.: PCT/US93/10756

§ 371 Date: Jun. 30, 1995

§ 102(e) Date: Jun. 30, 1995

[87] PCT Pub. No.: WO94/11494

PCT Pub. Date: May 26, 1994

Related U.S. Application Data

[63] Continuation of Ser. No. 973,832, Nov. 9, 1992, abandoned.
[51] Int. Cl.$^6$ .............................. C07H 21/04; C12N 15/85
[52] U.S. Cl. ...................... 536/24.5; 435/172.3; 435/325
[58] Field of Search .............................. 536/24.5; 514/44; 436/172.3, 325

[56] References Cited

U.S. PATENT DOCUMENTS 5,585,479  12/1996  Hoke et al. .............................. 536/24.5

OTHER PUBLICATIONS

Rojanasakul Y. "Antisense oligonucleotide therapeutics: Drug delivery and targeting." Adv. Drug Delivery Rev. 18: 115–131, 1996.

Kuivaniemi H, et al. "Mutations in collagen genes: Causes of rare and some common diseases in humans." FASEB 5: 2052–2060, Apr. 1991.

Uhlmann E, et al. "Antisense oligonucleotides: A new therapeutic principle." Chemical Reviews 90 (4): 543–584, Jun. 1990.

Rossouw C, et al. DNA sequences in the first intron of the human pro–alpha1(I) collagen gene enhance transcription. JBC 262 (31): 15151–15157, Nov. 5, 1987.

Gura T. "Antisense has growing pains." Science 270: 575–577, Oct. 27, 1995.

Orkin S, et al. "Report and Recommendations of the Panel to Assess the NIH Investment in Research on Gene Therapy." Dec. 7, 1995.

Helen e C, et al. "Specific regulation of gene expression by antisense, sense and antigene nucleic acids." Biochimica et Biophysica Acta 1049: 99–125, 1990.

Ala–Kokko, L. et al., 1991, "Hepatic fibrosis in rats produced by carbon tetrchloride and dimethylnitrosamine: observations suggestin immunoassays of serum for the 7S fragment of type IV collagen are a more sensitive index of liver damage than immunoassays for the NH2–terminal propeptide of type III procollagen," *Hepatology* 16(1):167–172.

Byers, P.H., 1990, "Brittle bones–fragile molecules: disorders of collagen gene structure and expressio n," *Trends Genet* 6(9):293–300.

Chang, E.H. et al., 1991, "Antisense inhibition of ras p21 expresion that is sensitive to a point mutation," *Biochemistry* 30(34):8283–8286.

Chiang, M.Y. et al., 1991, "Antisense of oligonucleotides inhibit intercellular adhesion moecule 1 expression by two distinct mechanisms," *J. Biol. Chem.* 266(27):18162–18171.

Chomczynski, P. et al., 1987, "Single–step method of RNA isolation by acid guanidinium thiocyanate–phenol–chloroform extraction," *Anal Biochem* 162(1):156–159.

Chu, M.L. and Prockop, D.J., *Extracellular Matrix Inherited Disorders of Connective Tissue*, Royce and Steinmann, Eds., Alan R. Liss, New York, 1992.

Erickson, R.P. and Izant, J.G., *Gene Regulation: Biology of Antisense RNA and DNA*, vol. 1, Raven Press, New York, 1992.

Horton et al., "Antisense regulation of human type II collagen synthesis," *The American Journal of Human Genetics* 51(4), Abstract 1505, 1992.

Khillan, J.S. et al., 1991, "Transgenic mice that express a mini–gene version of the human gene for type I procollagen (COL1A1) develop a phenotype resembling a lethal form of osteogenesis imperfecta," *J. Biol. Chem.* 266(34):23373–23379.

Kole, R. et al., 1991, *Adv. Drug Delivery Rev.* 6;271–286.

Kuivaniemi, H. et al., 1991, "Mutations in collagen genes: causes of rare and some common diseases in humans," *FASEB J* 5(7):2052–2060.

Marmur, J. and Doty, P., 1962, *J. Mol. Biol.* 5:113.

Mooslehner, K. and Harbers, K., 1988, "Two mRNAs of mouse pro α–I collagen gene differ in teh size of the 3'–untranslated region", *Nucleic Acids Research* 16(2):773.

Munroe, S.H., 1988, "Antisense RNA inhibits splicing of pre–mRNA in vitro," *EMBO J* 7(8):2523–2532.

Myers et al., 1988, *Proc. Natl. Acad. Sci. USA* 78:3516.

Olsen et al., 1991, *J. Biol. Chem.* 266:1117–1121.

Orkin, S., *The Molecular Basis of Blood Diseases*, G. Stamatoyannopoulos et al., Eds., W.B. Saunders, Philadelphia, 1987, pp. 106–126.

(List continued on next page.)

*Primary Examiner*—David T. Fox
*Assistant Examiner*—Amy J. Nelson
*Attorney, Agent, or Firm*—Pennie & Edmonds LLP

[57] ABSTRACT

The present invention is directed to oligonucleotides that inhibit mutant COL1A1 and/or wild type COL1A1 gene expression. The present invention is further directed to methods of inhibiting mutant and/or wild type collagen gene expression using the disclosed inhibitory oligonucleotides. The oligonucleotides and methods of the present invention are useful for the treatment of mammals having diseases related to inappropriate mutant or wild type COL1A1 gene expression.

7 Claims, 3 Drawing Sheets

OTHER PUBLICATIONS

Prockop, D.J., 1990, "Mutations that later the primary structur of type I collagen. The perils of a system for generating large structures by the principles of nucleated growth," *J. Biol. Chem.* 265(26):15349–15352.

Stacey, A. et al., 1988, "Perinatal lethal osteogenesis imperfecta in transgenic mice bearing an engineered mutant pro–α I collagen", *Nature* 332:131–136.

Stein, C.A. and Cohen, J.S. et al., Oligodeoxynucleotides as inhibitors of gene expression: a review, *Cancer Research* 48:2659–2668, 1988.

Sykes, B., 1990, "Human genetics. Bone disease cracks genetics," *Nature 348*:18–20.

Uhlmann et al., 1990, "Antisense Oligonucleotides: a new therapeutic principle," *Chemical Reviews 90(4)*:544–579.

Vandenberg, P. et al., 1991, "Expression of a partially deleted gene of human type II procollagen (COL2A1) in transgenic mice produces a chondrodysplasia," *Proc. Natl. Acad. Sci. U.S.A. 88(17)*:7640–7644.

Vu and Hirschbein, 1991, *Tetrahedron Letters* 32:3005–3008.

Vuorio et al., 1990, "The Family of Collegen Gene," *Ann. Rev. Biochem 59*:837–872.

Westefflausen, A., 1991, *Matrix. Col. Rel. Res.* 11:375–379.

Williams, C.J. and Prockop, D.J., 1983, "Synthesis an drpocessing of a type I procollagen containing shortened pro–α(I) chains by fibroblasts from a patient with osteogenesis imperfecta", *J. Biol Chem* 258(9):5915–5912.

ANTISENSE OLIGONUCLEOTIDES TO INHIBIT EXPRESSION OF MUTATED AND WILD TYPE GENES FOR COLLAGEN

CROSS REFERENCE TO RELATED APPLICATIONS

This application is the U.S. National Stage application of PCT application U.S. 93/10756 filed Nov. 9, 1993, which is a continuation application of U.S. Ser. No. 07/973,332 filed Nov. 9, 1992, now abandoned.

BACKGROUND OF THE INVENTION

Over 100 different mutations in genes for fibrillar collagens have been shown to cause genetic diseases. Byers, P. H., *Trends Genet.* 1990, 6, 293–300; Sykes, B., *Nature* 1990, 348, 18–20; Prockop, D. J., *J. Biol. Chem.* 1990, 265, 15349–15352; Kuivaniemi, H. et al., *FASEB J.* 1991, 5, 2052–2060. Moreover, the sequence of certain human collagen genes are known. Myers et al., *Proc. Natl. Acad. Sci. USA* 1988, 78, 3516, reported structure of a cDNA for the proα2 of human type I procollagen and, subsequently, the structures of a series of collagen genes have been defined (see Vuorio, E. and de Crombrugghe, B., *An. Rev. Biochem.* 1990, 58, 837–875; Chu, M.- L. and Prockop, D. J., *Extracellular Matrix and Inherited Disorders of Connective Tissue*, Royce and Steinmann, Eds., Alan R. Liss, New York, 1992). Mutations in either of the two genes for type I procollagen (COL1A1 and COL1A2) cause osteogenesis imperfecta and a subset of osteoporosis; mutations in the gene for type II procollagen (COL2A1) cause chondrodysplasias and some forms of osteoarthritis; and mutations in the gene for type III procollagen (COL3A1) cause Ehlers-Danlos syndrome type IV and aneurysms. Most of the mutations of procollagen genes produce disease phenotypes by directing synthesis of structurally abnormal but partially functional proα chains of type I, type II or type III procollagen. The partially functional proα chains associate with and become disulfide-linked to normal proα chains. As a result, the mutant chains can have one of several major effects. Kuivaniemi, H. et al., *FASEB J.* 1991, 5, 2052–2060. One effect is to prevent folding of the three chains into a collagen triple helix and thereby cause degradation of both the abnormal and normal proα chains through a process referred to as procollagen suicide. The second effect is to produce minor changes in the conformation of the collagen triple helix and thereby generate mutated monomers that interfere with self-assembly of normal monomers synthesized by the same cells.

A third effect of mutations in collagen genes is to decrease the amounts of collagen synthesized by fibroblasts and related cells. Mutations that decrease collagen synthesis, however, cause the relatively mild disease known as type I osteogenesis imperfecta. Deleterious effects of mutant collagen gene expression have been demonstrated in transgenic mice expressing mutated genes for type I procollagen. These transgenic mice developed phenotypes resembling human osteogenesis imperfecta, Stacey, A. et al., *Nature* 1988, 332, 131–136; Khillan, J. S. et al., *J. Biol. Chem.* 1991, 266, 23373–23379. Further, it has been demonstrated that transgenic mice expressing mutated genes of type II procollagen developed phenotypes resembling human chondrodysplasia. Vandenberg et al., *Proc. Natl. Acad. Sci.* 1991, 88, 7640–7644.

Since many heritable diseases of collagen are caused by the protein products from the mutated genes, it is believed that selective inhibition of expression of the mutated genes will be useful as a therapy for such diseases. Clinical observations have demonstrated that many patients with severe diseases caused by mutations in a collagen gene would benefit from selective inactivation of the mutant allele which directs the synthesis of mutant proα chains. The diseases in which selective inhibition may be useful include osteogenesis imperfecta, chondrodysplasia, certain forms of osteoporosis, certain forms of aneurysms, and certain forms of osteoarthritis.

In addition, it has been recognized for many decades that many pathological conditions are caused by overproduction of collagen fibers in the forms of scars and excess fibrous tissues. For example, liver cirrhosis is a two-step process in which normal liver tissue is first destroyed by a virus or by alcohol and other toxins, and then excessive amounts of collagen fibers replace the damaged cells before normal liver cell regeneration. Idiopathic pulmonary fibrosis is a lethal condition in which, for largely unknown reasons, normal lung tissue is gradually replaced by excessive amounts of collagen fibers. Progressive systemic sclerosis (scleroderma) is a frequently lethal disease where, again for unknown reasons, skin and many internal organs become leather-like because of excessive depositions of collagen fibers. In many individuals, wounds or surgical incisions in the skin are followed by excessive depositions of collagen in the form of hypertrophic scars and keloids that present cosmetic problems and sometimes more serious consequences. Also, excessive scarring frequently occurs in normal individuals following trauma and surgical procedures. In these and related conditions, a means of specifically inhibiting collagen synthesis and deposition would be of tremendous benefit. In addition, the same means of specifically inhibiting collagen synthesis and deposition would be useful in animal husbandry. For example, most horses develop large deposits of collagen fibers resembling human keloids and called "proud flesh" following injury to the legs that can limit the effective life of both draft horses and racing thoroughbreds.

It has been demonstrated that modified antisense oligonucleotides that are complementary to specific RNAs can inhibit the expression of a number of cellular and viral genes as proteins. See Erickson, R. P., and Izant, J. G. *Gene Regulation: Biology Of Antisense RNA And DNA*, Vol. 1, Raven Press, New York, 1992. For example, selective inhibition of a p21 gene that differed from a normal gene by a single nucleotide has been reported. Chang, E. H. et al., *Biochemistry* 1991, 30, 8283–8286. Moreover, mRNA splice junctions were suitable targets for antisense nucleic acids. Kole, R. et al., *Adv. Drug Delivery Rev.* 1991, 6, 271–286; Munroe, S. H. *EMBO J.* 1988, 7, 2523–2532. Many hypotheses have been proposed to explain the mechanisms by which antisense oligonucleotides inhibit gene expression, however, the specific mechanism involved may depend on the cell type studied, the RNA targeted, the specific site on the RNA targeted, and the chemical nature of the oligonucleotide. Chiang, M.-Y. et al., *J. Biol. Chem.* 1991, 266, 18162–18171; Stein, C. A., and Cohen, S., *Cancer Res.* 1988, 48, 2659–2668.

While there is a long felt need for therapies of disorders of collagen, such need has gone unmet. Methods to selectively decrease expression of either a normal allele or a mutant allele of collagen using antisense oligonucleotides would be of tremendous benefit to those suffering from diseases of collagen.

SUMMARY OF THE INVENTION

Mutations in genes encoding procollagen cause osteogenesis imperfecta, chondrodysplasia and related disorders, and Ehlers-Danlos syndrome type IV. They also cause a subset of osteoporosis, a subset of osteoarthritis and a subset of aneurysms. However, therapeutic and pharmacologic agents for the treatment of genetic diseases of collagen are few, and none involve the selective inhibition of the expression of the mutant collagen gene causing the disease. Also, excess synthesis and deposition of collagen in the form of scars and fibrous tissue causes most of the deleterious effects of diseases such as liver cirrhosis, pulmonary fibrosis, scleroderma, hypertrophic scarring and keloid formation. Also, excessive scarring frequently occurs in normal individuals following trauma and surgical procedures. The present invention provides a means based on antisense strategies to inhibit selectively expression of either a mutated or a normal gene for collagen. Therefore, it provides a means for preventing or reversing many of these conditions.

To investigate the selective inhibition of expression of a mutant collagen gene, modified antisense oligonucleotides complementary to an exogenous mutated COL1A1 gene were prepared. In the test system, the exogenous gene consisted of a construct of the human COL1A1 gene which was transfected into mouse cells. As a result, the mouse cells synthesized mutated proα1 (I) chains of human type I procollagen. The mouse cells also synthesized normal proα1 (I) chains of mouse type I procollagen from the endogenous mouse COL1A1 gene. The modified antisense oligonucleotides were designed to contain a base sequence that was complementary to and that, therefore, would bind to a target sequence in RNA transcripts of the exogenous human COL1A1 gene. In the example provided here, the target sequence was 20 nucleotides from exon 1 and intron 1 of the normal human COL1A1 gene that differed by 9 nucleotides in the same sequence of the normal mouse COL1A1 gene. When the modified oligonucleotide was applied to transfected cells expressing both the exogenous human COL1A1 gene and the endogenous mouse COL1A1 gene, expression of the human COL1A1 gene was specifically inhibited. The inhibition of the human COL1A1 gene ranged from 50 to 80%, with less than 10% inhibition of expression of the endogenous mouse gene for the same collagen or the endogenous mouse gene for the related extracellular protein called fibronectin.

Missense and sense versions of the same oligonucleotide had essentially no effect on expression of the exogenous gene. The inhibition observed with the most effective oligonucleotide was reduced by introducing a single base change in the oligonucleotide. Selective inhibition of expression of the exogenous collagen gene was consistently observed in all experiments. In the presence of lipofectin that was used as a carrier for the oligonucleotide, the concentration of oligonucleotide required for effective inhibition was as low as 0.1 μM. Therefore, these results indicate that the same oligonucleotide or a modified form of the same oligonucleotide will be useful to rescue the phenotype of fragile bones in transgenic mice expressing the same internally deleted gene or similar deleted genes. Further, it is believed that certain other oligonucleotides designed to bind other mutant collagen genes may be useful to inhibit mutant collagen gene expression in mammals, including humans.

In addition, oligonucleotides designed to target sequences in normal collagen genes may be useful in diseases and related conditions in which deleterious effects are produced by excessive synthesis and deposition of collagen in tissues.

Oligonucleotides complementary to specific sequences in either the human COL1A1 gene or the mouse COL1A1 gene are provided.

Methods are also provided for selecting and preparing the oligonucleotides. Further, methods are included in the invention for treating mammals having diseases or related conditions caused by expression of mutated gene for collagen or caused by excessive expression of normal collagen genes in response to injury to specific tissues.

The methods of the invention will be particularly useful to treat humans suffering from diseases of collagen by selective inhibition of mutant collagen gene expression using oligonucleotides of the invention. They will also be useful to treat humans and other mammals suffering from diseases and related conditions caused by excessive synthesis and deposition of normal collagen in tissues, i.e., condition such as liver cirrhosis, pulmonary fibrosis, scleroderma and scarring following trauma or surgery.

DETAILED DESCRIPTION OF THE INVENTION

Figure 1:
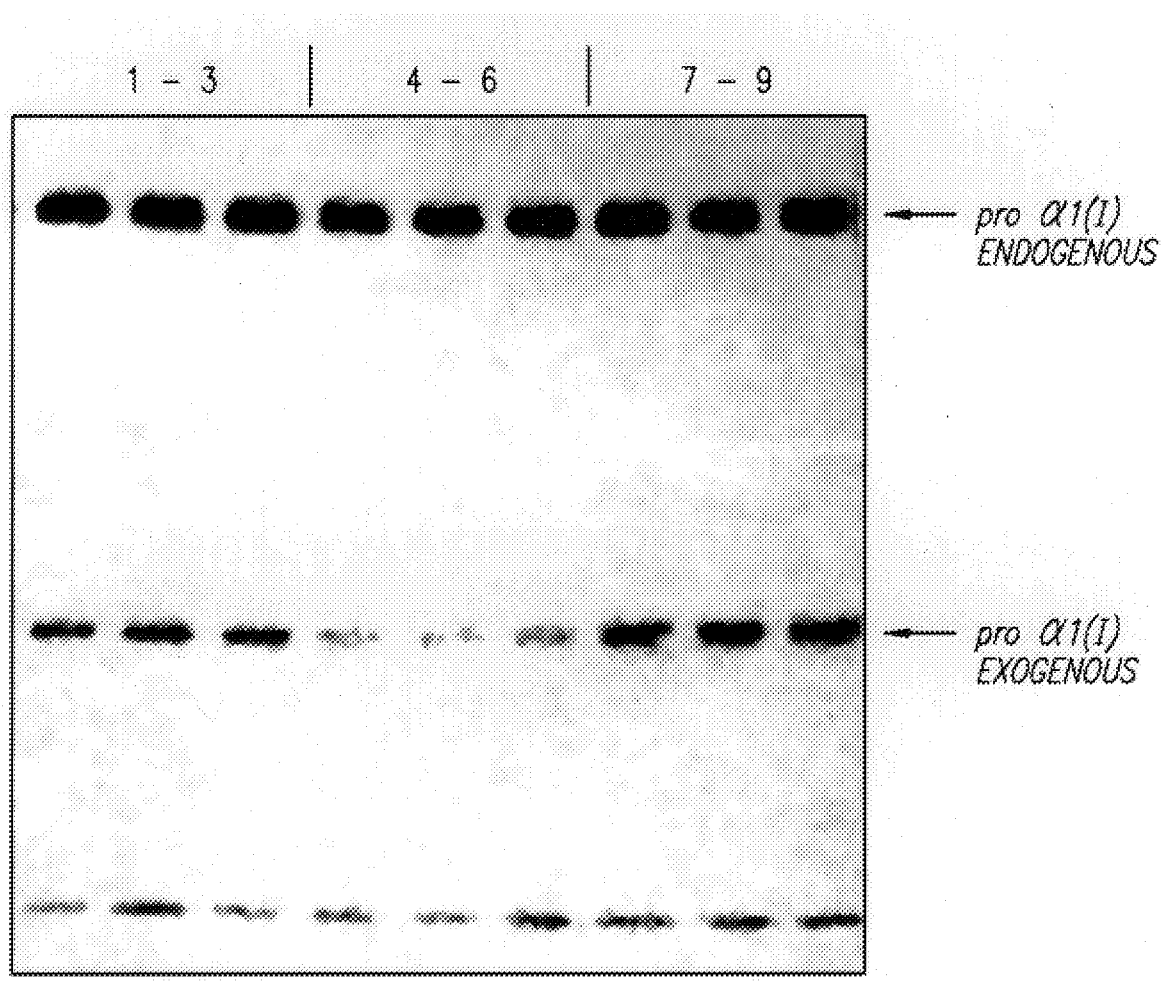
FIG. 1 shows Western blot assays of expression of the endogenous gene (SEQ ID NO: 4) and the exogenous gene (SEQ ID NO: 3) for proα1 (I) chains (COL1A1). Lanes 1 to 3: Cells treated with missense oligonucleotide MS3 (SEQ ID NO: 6). Lanes 4 to 6: Cells treated with the antisense oligonucleotide AS3 (SEQ ID NO: 5). Lanes 7 to 9: Control cells not treated with oligonucleotides. Three samples of cells were treated identically and analyzed separately in the lanes shown.

It has been established that many of the genetic mutations of fibrillar collagens produce disease phenotypes because they cause synthesis of structurally abnormal but partially functional proα chains of type I, type II or type III procollagen. It has further been established that mutations in procollagen genes cause osteogenesis imperfecta, chondrodysplasia and Ehlers-Danlos syndrome. Mutations in the same genes also cause some subsets of osteoporosis, osteoarthritis, and familial aneurysms. However, effective therapies have been lacking for disorders arising from mutant collagen production. The present invention concerns oligonucleotides useful for inhibition of mutant collagen gene expression, and provides methods using these compounds for treatment of disorders caused by mutant collagen gene expression. It also concerns oligonucleotides useful for inhibition of expression of normal collagen genes to prevent excessive deposition of collagen in fibrotic conditions.

The invention provides an oligonucleotide substantially complementary to a mutant collagen nucleotide sequence or a normal collagen nucleotide sequence. "Nucleotide sequence" refers to a polynucleotide formed from a series of joined nucleotide units. The term "substantially complementary", as used herein, refers to that amount of complementarity between the oligonucleotide and a collagen nucleotide sequence which allows for potentially stable interstrand hybridization and enables the oligonucleotide to inhibit the expression of the collagen gene. Interstrand hybridization is the interaction between the oligonucleotide and the collagen nucleotide sequence. The potential capability of forming a stable interstrand hybrid can be determined by those skilled in the art using methods known in the art, such as, for example, determination of the melting temperature for the hybrid ($T_m$) by mathematical modelling or empirical analysis, solid support nucleic acid hybridizations, or $C_o t$ analysis. (Marmur, J. and Doty, P., *J. Mol. Biol.* 1962, 5, 113).

As used herein, the term "collagen nucleotide sequence" refers to any nucleotide sequence derived from a wild type or mutant collagen or procollagen gene, including, for example, DNA or RNA sequence, DNA sequence of the gene, any transcribed RNA sequence, RNA sequence of the pre-mRNA or mRNA transcript, and DNA or RNA bound to protein.

Oligonucleotides useful for inhibition of mutant collagen gene expression may be selected by comparing a mutant collagen nucleotide sequence with a wild type collagen nucleotide sequence. A region of the mutant collagen nucleotide sequence comprising at least one nucleotide difference from the wild type collagen nucleotide sequence may be selected as the target for the oligonucleotide. An oligonucleotide complementary to this region is expected to be able to selectively hybridize to the mutant collagen nucleotide sequence but not the wild type nucleotide sequence.

In addition, neutral variations in the base sequence of an allele for a gene can be used as a target site for the oligonucleotide. Therefore, a panel of oligonucleotides to normal alleles can be used to inhibit expression of an allele that contains a neutral variation in sequence and a disease-causing mutation at a second site in the same allele, the use of a panel of oligonucleotides to normally functioning alleles will greatly reduce the number of specific oligonucleotides needed, since it will not be necessary to design a new oligonucleotide for each new mutation that is discovered in a given gene.

Oligonucleotides targeted to invariant sequences in collagen genes can be used to inhibit collagen synthesis in fibrotic conditions.

The oligonucleotide may be any length of sequence potentially capable of forming a stable hybrid with the mutant or normal collagen nucleotide sequence. The potential capability of forming a stable hybrid can be determined by those skilled in the art using methods known in the art. It is preferred that the length of the oligonucleotide be between 5 and 200 nucleotides. It is more preferred that the oligonucleotide be between 10 and 50 nucleotides in length. It is most preferred that the oligonucleotide be between 15 and 25 nucleotides in length.

The nucleotides of the oligonucleotides may be those known in the art such as natural and synthetic moieties. The term "oligonucleotide" as used herein refers to a polynucleotide formed from joined nucleotides. Moreover, the term "oligonucleotide" includes naturally occurring oligonucleotides or synthetic oligonucleotides formed from naturally occurring subunits or analogous subunits designed to confer special properties on the oligonucleotide so that it is more stable in biological systems or binds more tightly to target sequences. It also includes modifications of the oligonucleotides such as chemically linking them to other compound that will enhance delivery to cells or to the nucleus and other compartments of cells. The term "wild type" as used herein refers to the a natural, functional form of a collagen or procollagen nucleotide sequence. This includes, for example, natural, functional genes and transcripts of procollagen types I to XVI and to still undiscovered collagens that may be found in tissues of mammals.

Oligonucleotides substantially complementary to regions of the mutant nucleotide sequence that comprise a variation from the wild type nucleotide sequence of at least one point mutation, missense mutation, nonsense mutation, deletion, recombination, insertion or combinations of such mutations are preferred in the invention. Normal invariant sequences are preferred to applications involving the inhibition of normal collagen synthesis and deposition.

A preferred embodiment of the invention is an oligonucleotide complementary to mutant or normal wild type nucleotide sequence of type I procollagen (COL1A1 and COL1A2), type II procollagen (COL2A1), type III procollagen (COL3A1) or type IV collagen (COL4A1, COL4A2, COL4A3, COL4A4 and COL4A5). It is further preferred that the oligonucleotide be complementary to a nucleotide sequence derived or selected from a mammal, in particular, a human.

The oligonucleotides of the present invention may be oligodeoxyribonucleotides or oligoribonucleotides, including modified oligodeoxynucleotides and oligoribonucleotides. Moreover, the oligonucleotides of the invention may be comprised of combinations of deoxyribonucleotides and ribonucleotides.

Further, oligonucleotides of the invention may also include modified subunits. For example, the invention may include phosphorothioate oligodeoxyribonucleotides.

It is preferred that the oligonucleotides of the invention be modified to increase stability and prevent intracellular and extracellular degradation. It is more preferred that the oligonucleotides of the invention be modified to increase their affinity for target sequences, and their transport to the appropriate cells and cell compartments when they are delivered into a mammal in a pharmaceutically active form.

Oligonucleotides of the invention may be synthesized by any method known in the art. It is preferred in the present invention that the oligonucleotides be prepared using synthetic chemical methods, such as, for example, phosphoramidite chemistry by sulfurization with tetraethylthiuram disulfide in acetonitrile. See, for example, Vu and Hirschbein, *Tetrahedron Lett.* 1991, 32, 30005–30008. Oligonucleotides of the invention may also be synthesized using in vitro and in vivo transcription systems, such as transcription by T7 polymerase or expression vectors. Oligonucleotides synthesized using in vitro and in vivo transcription systems may be modified via chemical methods known to those skilled in the art. Examples of such modifications include encapsulation in liposomes, or chemical linkage to steroids, antibodies, and cell receptors.

It is preferred that an oligonucleotide substantially complementary to a mutant or wild type collagen nucleotide sequence comprises a collagen gene expression control sequence. The term "gene expression control sequence", as used herein, denotes sequences that affect the level of expression of a gene. Gene expression control sequences that affect the level of translation or the rate of RNA processing are preferred, but the invention is not limited to sequences involved in these processes. Gene expression control sequences useful in the invention include, for example, 5'- and 3'-splice junction sequence, splicing branchpoint sequence, small nuclear ribonucleoprotein binding site sequence (snRNP), polyadenylation region sequence, translation initiation region sequence, transcript 5'- and 3'-untranslated region sequence, and sequence affecting RNA turnover. The translation initiation site may include the Kozak sequence or other sequence embedding the start codon or adjacent to the start codon. The 5'-splice junction sequence may include the U1 snRNP binding site or the 5'-splice junction octanucleotide consensus sequence. Moreover, the 5'-splice junction sequence may include sequences embedding the splice junction or adjacent to the splice junction. The 3'-splice junction sequence may include sequences embedding the splice junction or adjacent to the splice junction. The polyadenylation region sequence may include the AAUAAA consensus hexanucleotide, and active variants thereof, and sequences surrounding the cleavage site or adjacent to the cleavage site. The target sequences for the oligonucleotides shall also include sequences that code for amino acid sequences in the proteins.

It is preferred that the oligonucleotides of the invention be antisense oligonucleotides. It is more preferred that the oligonucleotides of the invention be targeted to a collagen gene splice junction, in particular, a 5'-splice junction. Herein, the term "splice junction" may encompass a 5'-splice junction sequence including the U1 snRNP binding site or the 5'-splice junction octanucleotide consensus sequence, or a 5'-splice junction sequence including sequences embedding the splice junction or adjacent to the splice junction. The term "splice junction may also denote a 3'-splice junction sequence including sequences embedding the splice junction or adjacent to the splice junction. The splice junction of the invention may be, for example, an activated cryptic splice junction, a splice junction reconstituted at a deletion junction, or reconstituted by some other mutation, or a dominant splice junction within a mutated sequence milieu. Another preferred method of the inventions is oligonucleotides targeted to coding sequences of the gene.

The invention further includes an oligonucleotide substantially complementary to a mutant collagen splice junction comprising SEQ ID NO: 18. This consensus sequence is derived from a number of oligonucleotides tested which exhibit certain degrees of inhibitory activity on mutant collagen gene expression. See Tables 1 and 2.

To demonstrate the usefulness of the oligonucleotides of the invention, mouse NIH 3T3 cells stably transfected with an internally deleted "mutant" construct of the human COL1A1 gene which encodes shortened proα1 (I) chains of type I procollagen were contacted with the oligonucleotides. These oligonucleotides were synthesized using a region at the 3' end of exon 1 and the first two nucleotides of intron 1 of the exogenous human gene as a target. See Table 1. The target site was selected because the human gene contained 27 nucleotides in exon 1 that were not found in the corresponding endogenous mouse gene. Cells contacted with the oligonucleotides showed selective inhibition of the mutant COL1A1 gene. See Examples 5 through 8. The target sequence of the most effective oligonucleotide tested was a 20 nucleotide stretch. This human collagen target sequence differed from the mouse sequence by nine nucleotides. The observed effects on expression were specific and ranged from 50 to 80% inhibition of the exogenous gene. Less than 10% inhibition of expression of the endogenous collagen gene or the fibronectin gene was observed. To further demonstrate the specificity of these oligonucleotides, missense or sense versions of the same oligonucleotide were tested. These oligonucleotides had essentially no effect on target gene expression. Also, the inhibition observed with the most effective oligonucleotide tested was reduced by introducing a single base change.

It is evident from the forgoing illustration that the oligonucleotides of the invention are useful for research as research reagents. However, the oligonucleotides can also be used as diagnostic and therapeutic agents, and in kits.

The invention also includes an oligonucleotide which comprises a sequence selected from the group of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:19, SEQ ID NO:20, SEQ ID NO:21, SEQ ID NO:22 and SEQ ID NO:23. See Tables 1 and 2. Certain of these oligonucleotides are complementary to the mutant 5'-splice junction sequence and effectively inhibit expression of the mutant exogenous gene. See Table 2. Oligonucleotides having SEQ ID NO:5, SEQ ID NO:8, SEQ ID NO:19, SEQ ID NO:20, SEQ ID NO:21, SEQ ID NO:22 and SEQ ID NO:23 are particularly inhibitory. Oligonucleotides of the foregoing group are particularly useful as research reagents while not being limited to such use.

It is expected that the oligonucleotides of the invention will be useful in pharmaceutical preparations for therapeutic purposes when delivered to mammals, particularly humans. Provided are pharmaceutical compositions for inhibiting mutant and normal collagen gene expression comprising an oligonucleotide of the invention, and a pharmaceutically acceptable carrier or diluent.

The invention further provides a preferred embodiments of pharmaceutical compositions comprising an oligonucleotide substantially complementary to a mutant or normal collagen gene expression control sequence, such as a collagen gene splice junction.

Pharmaceutical compositions comprising an oligonucleotide having SEQ ID NO: 18 are also included.

The pharmaceutical compositions comprising the oligonucleotides may be administered orally in solid dosage forms, such as capsules, tablets, and powders, or in liquid dosage forms, such as elixirs, syrups, and suspensions. They may also be administered parenterally in sterile liquid dosage forms as well as by inhalation or topical administration.

The dosage administered varies depending upon factors such as: pharmacodynamic characteristics; its mode and route of administration; age, health, and weight of the recipient; nature and extent of symptoms; kind of concurrent treatment; and frequency of treatment. Effective dosages are those which are able to inhibit collagen protein production in cells at a level which eliminates or reduces the symptons or conditions associated with the collagen portein production.

The compounds may be formulated with a pharmaceutically acceptable topical carrier and the formulation to produce a creme, lotion or ointment for example.

For parenteral administration, the oligonucleotides of the invention may be mixed with a suitable carrier or diluent such as water, an oil, saline solution, aqueous dextrose, and other sugar solutions, glycols such as propylene glycol or polyethylene glycols, and lipids such as in liposomes or cationic lipids capable of binding nucleic acid.

Further, a water soluble salt of an oligonucleotide of the invention may be used for parenteral administration. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

Solutions for parenteral administration comprise preferably an oligonucleotide of the invention encapsulated in or bound to a cationic lipid.

As a demonstration of the effectiveness of compositions comprising lipid, lipofectin was tested in a cell culture system. Lipofectin optimized inhibition for all of the antisense oligonucleotides tested. See Example 5, Tables 2 and 3, and Example 8, Table 4. The concentration of oligonucleotide required for effective inhibition were as low as 0.1 $\mu$M which is a physiologically acceptable concentration for mammalian therapeutic agents. In view of this observation it is expected that the oligonucleotides of the invention will be useful for treatment of mammals.

The oligonucleotides of the invention may be administered by any method that produces contact of the oligonucleotide with the oligonucleotide's site of action in the body of a mammal including but not limited to oral, intravenous, and intraparenteral.

The oligonucleotides may be administered singly, or in combination with other compounds of the invention, other pharmaceutical compounds, or therapies. The oligonucleotides are preferably administered with a pharmaceutically acceptable carrier or diluent selected on the basis of the selected route of administration and standard pharmaceutical practice.

The oligonucleotides of the invention are administered to mammals, preferably humans, in therapeutically effective amounts or concentrations which are effective to inhibit mutant collagen gene expression, or to treat diseases exhibiting mutant collagen gene expression. The dosage administered in any particular instance will depend upon factors such as the pharmacodynamic characteristics of the particular oligonucleotide of the invention, and its mode and route of administration; age, health, and weight of the recipient; nature and extent of symptoms; kind of concurrent treatment, frequency of treatment, and the effect desired.

Inhibition of aberrant collagen gene expression is a major focus of this invention. To achieve this end, the invention provides methods of inhibiting mutant collagen gene expression which comprise contacting a cell comprising the mutant collagen gene with a mutant collagen gene expression inhibitory amount of an oligonucleotide substantially complementary to a mutant collagen nucleotide sequence or a neutral variation in the sequence of the same collagen allele containing the mutant sequence and not perfectly complementary to a wild type collagen nucleotide sequence or the target sequence in the allele for the wild type collagen allele. The invention also includes a method whereby the contacting step comprises lipofectin as a carrier for the oligonucleotide. In addition, the invention includes similar methods for inhibiting expression of wild type collagen genes.

Moreover, a method of inhibiting mutant or wild type collagen gene expression is provided wherein the collagen nucleotide sequence comprises a collagen gene expression control sequence, such as a collagen gene splice junction, particularly a 5'-splice junction or a normal coding sequence.

Also included is a method of inhibiting collagen gene expression wherein the oligonucleotide comprises a sequence selected from the group of SEQ ID NO: 5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:19, SEQ ID NO:20, SEQ ID NO:21, SEQ ID NO:22 and SEQ ID NO:23. See Table 2. Methods comprising these oligonucleotides are particularly useful in research while not being limited to such use.

A further method of inhibiting mutant and wild type collagen gene expression is included wherein the oligonucleotide comprises SEQ ID NO: 18.

As a demonstration of this method for inhibiting collagen gene expression, mouse NIH 3T3 cells stably expressing an internally deleted version of the human COL1A1 gene were grown in cell culture. The utility of the system was that it made it possible to assay directly changes in the expression of the exogenous human COL1A1 relative to the expression of the endogenous mouse COL1A1. Specifically, the exogenous human COL1A1 had an internal deletion of 40 exons (exons 6 to 45) engineered so that the mRNA and the proα1 (I) chains synthesized from the gene were less than half the size of the MRNA and proα1 (I) chains synthesized from the mouse endogenous COL1A1 gene. Hence, specific inhibition of one gene relative to the other was readily assayed in the same sample of cells or tissues with techniques employed by those familiar in the art.

The cells were plated at a concentration adjusted to obtain subconfluent cultures at the end of the experiment. After twenty hours the cells were washed two times with prewarmed medium, and treated with lipofectin. Oligonucleotides dissolved in distilled water were then added and the cells were incubated. Media comprising heat inactivated calf serum and antibiotic were then added. The cells were then incubated for the additional times indicated in the Examples. RNA and protein analyses demonstrated that contacting cells expressing the mutant human collagen gene with certain oligonucleotides of the invention using the above method significantly inhibited the mutant gene expression. See Example 5, Tables 2 and 3, and Example 8, Table 4. Maximal inhibition with AS3 (SEQ ID NO: 5) was observed in about 20 hours. See FIG. 3. The inhibition began after 8 hours and persisted for at least 30 hours.

The mutated human COL1A1 gene used in these experiments with cells was modeled after a mutated COL1A1 gene shown to cause a lethal form of osteogenesis imperfecta. Williams, C. J. and Prockop, D. J., *J. Biol. Chem.* 1983, 258, 5915–5921; and Olsen et al., *J. Biol. Chem.* 1991, 266, 1117–1121. The same mutated human COL1A1 gene was used to prepare transgenic mice. Lines of transgenic mice expressing high levels of the gene were shown to develop fractures of bones similar to those seen in children with osteogenesis imperfecta. Khillan, J. S. et al., *J. Biol. Chem.* 1991, 266, 23373–23379. Therefore, oligonucleotides that inhibit the expression of the mutated human COL1A1 gene in cell culture offer the potential of inhibiting expression of the same mutated human COL1A1 gene in the transgenic mice and thereby rescuing the phenotype of fragile bones in the transgenic mice. Successful testing of the oligonucleotides in the transgenic mice would offer the prospect of using the same or similar oligonculeotides to treat or prevent fragile bones in children with osteogenesis imperfecta. Since mutations in the COL1A1 gene are a cause of a subset of post-menopausal osteoporosis, the same or similar oligonucleotides may be useful in treating or preventing osteoporosis. Of special importance is that the same cells and transgenic mice expressing the mutated human COL1A1 gene can be used to develop oligonucleotides to specifically inhibit expression of normal human COL1A1 genes by targeting either invariant sequences in the human gene or regions that contain neutral variations in normal alleles of genes.

The oligonucleotides of the invention will be capable of reaching their intracellular target to affect inhibition of mutant collagen gene expression. The invention therefore provides methods of inhibiting mutant and wild type collagen gene expression which comprise contacting at least one element of gene expression machinery with a collagen gene expression inhibitory amount of an oligonucleotide. For the purposes of the invention, the elements of the gene expression machinery may comprise any nucleotide sequence of a gene, the nucleotide sequence of spliced mRNAs transcribed from a gene, unspliced RNAs and partially spliced RNAs transcribed from a gene, DNA-RNA hybrids comprising sequence derived from a gene, such as in actively transcribing genes, RNA transcribed from a gene bound to protein, and any molecule or structure known in the art to be involved in gene expression.

Further, the oligonucleotides of the invention will be capable of inhibiting collagen gene expression in cells in vivo and in vitro, including, for example, individual cells, cells comprising tissues, cells comprising organs, and cells comprising organisms. The inhibitory effect of an oligonucleotide ranges from the lowest statistically significant inhibitory level to about 100% inhibition. Using the methods of the invention, one skilled in the art will be able to design or select oligonucleotides which are appropriate for the degree of inhibition which is needed for the desired purpose without undue experimentation.

An important aspect of the invention is the use of the oligonucleotides of the invention in the treatment of disease since there are few effective therapies for collagen disorders. The invention includes a method for treating a disease exhibiting mutant collagen gene expression which comprises administering to a mammal suffering from a disease caused by expression of a mutant collagen gene, an inhibitory amount of an oligonucleotide substantially complementary to a mutant collagen nucleotide sequence and not perfectly complementary to mutant collagen nucleotide sequence. Alternatively, the inhibitory oligonucleotide can be substantially complementary to a neutral sequence variation found in the same collagen allele containing the mutation but not substantially complementary to the same target site in the second allele for the same collagen in the same individual. The methods of the invention also include administering to a mammal suffering from a fibrotic condition, an inhibitory amount of an oligonucleotide substantially complementary to an invariant sequence in the wild type sequence of a neutral variant sequence in the wild type gene to inhibit, specifically, expression of the gene and, thereby, prevent deleterious deposition of collagen in tissues. The methods of the invention also include the delivery of oligonucleotides to certain regions of the mammal being treated, such as, for example, by specific and targeted delivery of the oligonucleotides to certain organs or tissues, including bolus delivery and immunological targeting. Thus, pharmaceutical preparations comprising the oligonucleotides may be injected directly into a desired bodily site. Moreover, antibodies may be bound to the oligonucleotides or oligonucleotide-lipid complexes to direct the oligonucleotides to cells expressing certain antigens, such as virally infected cells. It is believed that the methods of the invention for treating disease are particularly useful in the treatment of human diseases of collagen, including, for example, osteogenesis imperfecta, chondrodysplasia and Ehlers-Danlos syndrome type IV. It is also believed they will be useful in treating subsets of patients with specific types of osteoporosis, osteoarthritis and aneurysms. It is also believed they will be useful in treating many patients with fibrotic conditions such as liver cirrhosis, pulmonary fibrosis, scleroderma, hypertrophic scar formation and keloids. It is also believed they will be useful in treating normal individuals to prevent fibrotic scarring following trauma or surgical procedures.

Moreover, the invention provides a preferred method of treatment wherein the mutant collagen nucleotide sequence comprises a collagen gene expression control sequence, such as a collagen gene splice junction.

Another method for treating a disease exhibiting mutant collagen gene expression is included wherein the oligonucleotide comprises SEQ ID NO: 18.

The usefulness of the oligonucleotides of the invention in the treatment of mammals can be seen from the concentrations of oligonucleotide sufficient to inhibit gene expression. The concentration of oligonucleotide required for effective inhibition was as low as 0.1 $\mu$M. See Example 8, Table 4. In view of this observation, it is expected that the same or similar oligonucleotides in a pharmaceutically acceptable carrier will be useful to rescue the phenotype of fragile bones in transgenic mice expressing the same internally deleted gene. It is also expected that these oligonucleotides will be useful to inhibit the expression of mutant collagen genes in collagen disorders of humans.

Since the oligonucleotide is specifically targeted to an invariant region of the wild type human COL1A1 gene, it is also expected that it will be useful in treating fibrotic conditions in man and other mammals.

The following examples are illustrative of the invention. It is understood that this invention is not limited by these illustrative examples but solely by the claims appended hereto.

EXAMPLES

Example 1 Oligonucleotide Synthesis

Phosphorothioate oligodeoxynucleotides were synthesized via phosphoramidite chemistry by sulfurization with tetraethylthiuram disulfide in acetonitrile. See Vu and Hirschbein, *Tetrahedron Lett.* 1991, 32, 3005–3008.

Example 2 Treatment of Cell Cultures

NIH 3T3 cells stably expressing an internally deleted version of the human COL1A1 gene, Olsen, A. S., *J. Bio. Chem.* 1991, 266, 1117–1121, were grown in Dulbecco's modified Eagle's medium (DMEM) containing 10% calf serum and 400 $\mu$/ml of Geneticin (GIBCO BRL, Gaithersberg, Md.). The cells were plated in 24-well plates (Falcon, Becton-Dickinson, New Lincoln, N.J.) at a concentration adjusted to obtain subconfluent cultures at the end of the experiment. Twenty hours later, the cells were washed two times with prewarmed DMEM, and 0.3 ml of DMEM containing the indicated concentration in lipofectin (GIBCO BRL, Gaithersberg, Md.) was added in each well. Oligonucleotides dissolved in distilled water were then added as a 20× stock solution and incubated for 4 hours at 37° C. About 0. 7 ml of DMEM containing 14% calf serum previously heat inactivated at 56° C. for 1 hour and 400 $\mu$g/ml of Geneticin were added. The cells were then incubated at 37° C. for the additional times indicated.

Example 3 Protein Analysis

At the end of incubation with the oligonucleotides, cells were washed two times in DMEM and solubilized in 0.1 ml of lysis buffer consisting of 1% SDS; 1% sodium deoxycholate; 0.1% Triton X-100; 10 mM EDTA; 0.5 units of aprotinin (Sigma, St. Louis, Mo.) per ml; 3% β-mercaptoethanol; and phosphate buffered saline (PBS) adjusted to pH 7.4. After 5 minutes incubation at room temperature, the cell lysate was harvested, strongly vortexed and one-fourth volume of sample loading buffer was added (0.6M Tris-HCl buffer, pH 6.8; 50% glycerol; 1% SDS; 0.012% bromphenol blue). The lysate was then heated for 5 minutes at 94° C. and 10 μl of the sample was electrophoresed on a 7.0% SDS polyacrylamide gel. Proteins were electrophoretically transferred to nitrocellulose filters (Schleicher and Schuell, Keene, N.H.) and reacted with an antibody against a synthetic peptide corresponding to the last 21 amino acids of human proα1 (I) chain of type I procollagen. The antibody recognized both the human and the mouse COOH-terminal propeptide of the proα1 (I) chain. Olsen, A. S., *J. Biol. Chem.* 1991, 266, 1117–1121.

The proα1(I) bands were detected by reaction with a goat anti-rabbit antibody coupled to $^{125}$I (Dupont-NEN, Boston, Mass.) and subsequent autoradiography. Relative amounts of protein from the endogenous and exogenous COL1A1 genes were then assayed by using a laser densitometer (LKB, Ultroscan XL, Piscataway, N.J.).

Example 4 RNA Assay

For RNA assays, total cellular RNA was isolated from tissues using acidic guanidine thiocyanate-phenol-chloroform extraction. Chomczynski, P., and Sacchi, M., *Anat. Biochem.* 1987, 162, 156–159. The ratio of mRNA from exogenous and endogenous genes was measured by a quantitative polymerase chain reaction (PCR) assay. Primers for reverse transcription and polymerase chain reaction were designed to be complementary to identical sequence in human and mouse proα1 (I) mRNA. Mooslehner, K., and Habers, K., *Nucl. Acids Res.* 1988, 16, 773; Westefflausen, A., *Matrix. Col. Rel. Res.* 1991, 11, 375–379. This strategy provided the same efficiency of amplification for both mRNAs. Five micrograms of total cellular RNA were reverse transcribed in 20 μl of reaction mixture using 200 pmol of the primer BS33 having the sequence 5'-ACTAAGTTTGA-3' (SEQ ID NO: 17) and a preamplification system for first strand cDNA synthesis (SuperScript™, GIBCO BRL, Gaithersberg, Md.). After RNase H treatment, cDNA was amplified by PCR (GeneAmp®, Perkin-Elmer Cetus, Norwalk, Conn.) using primer BS31 (5'-TTGGCCCTGTCTGCCT-3') (SEQ ID NO: 1) and $^{32}$P-labeled primer BS32 (5'-TGAATGCAAAGGAAAAAAAT-3') (SEQ ID NO: 2) at concentrations of 4 pmol per 100 μl of reaction mixture. PCR conditions were 1 minute 20 seconds at 94° C., 1 minute at 47° C., and 20 seconds at 72° C. for 15 cycles. Amplified products from human proα 1(I) mRNA and mouse proα1 (I) mRNA were 176 and 177 bp long, respectively, and were distinguishable only after digestion with BstN I. Ten microliters of PCR product were digested by 2 units of BstN I for 1 h at 60° C., denatured and electrophoresed in 15% PAGE containing 6M urea. The gel was fixed, dried and exposed to x-ray film.

Example 5 Initial Tests of Modified Oligonucleotides

To develop antisense oligonucleotides, the test system employed mouse NIH 3T3 cells stably transfected with an internally deleted construct of the human gene for the proα1 (I) chains of type I procollagen (COL1A1). See Prockop, D. J., *J. Biol. Chem.* 1990, 265, 15349–15352. A series of modified oligonucleotides were synthesized using a region at the 3' end of exon 1 and the first two nucleotides of intron 1 of the exogenous gene as a target (Table 1).

TABLE 1

DESIGN OF MODIFIED OLIGONUCLEOTIDES

A. DNA SEQUENCE AT THE EXON 1/INTRON 1 JUNCTION[a]

| | SEQ ID NO: |
|---|---|
| 200        210        220<br>•           •           •<br>5' CAAGTCGAGGGCCAAGACGAAGACAgt 3' | 3 |
| 3' GTTCAGCTCCCGGTTCTGCTTCTGTca 5'<br>  \|    \|    \|        \| \|\|\|\|\|\|\|\|\|\| | Exogenous |
| 5' CTCCTGACGCATGGCCAAGAAGACAgt 3' | 4 |
| 3' GAGGACTGCGTACCGGTTCTTCTGTca 5'<br>•           •           •<br>170        180        190 | Endogenous |

B. PHOSPHOROTHIOATE OLIGODEOXYNUCLEOTIDES

| CODE | SEQUENCE(5'–3') | TARGET | SEQ ID NO: |
|---|---|---|---|
| AS3 | ACTGTCTTCGTCTTGGCCCT | Exo (224–205) | 5 |
| MS3[b] | ATCCTGCTTCGTTCTGGCTC | Missense of AS3 | 6 |
| S3[c] | AGGGCCAAGACGAAGACAGT | Exo (205–224) | 7 |
| AS7[d] | ACTGT<u>A</u>TTCGTCTTGGCCCT | Exo (224–205) | 8 |
| AS8 | TGTCTTCGTCTTGGCCCTCG | Exo (222–203) | 9 |
| AS9 | TCTTCGTCTTGGCCCTCGAC | Exo (220–201) | 10 |
| AS10 | ACTGTCTTCGTCTTG | Exo (224–210) | 11 |
| AS11 | GTCTTGGCCCTCGACTTG | Exo (215–198) | 12 |
| AS12 | ACTGTCTTCTTGGCCATGCG | Endo (195–176) | 13 |
| AS14[e] | ACTGT<u>A</u>TTCTTGGCCATGCG | Endo (195–176) | 14 |
| AS15[e] | ACTGTCT<u>A</u>CTTGGCCATGCG | Endo (195–176) | 15 |
| AS16[d] | ACTGTCT<u>A</u>CGTCTTGGCCCT | Exo (224–205) | 16 |
| | ACTAAGTTTGA | | 17 |
| | NMNWCGNCNNG | | 18 |
| AS41 | ATCCGCGCCGAGGGCAACA | | 19 |
| AS28 | GTACCATGACCGAGACGTGT | | 20 |
| AS44 | GCTTCGACGTTGGCCCTGTC | | 21 |
| AS40 | ACAAGAGGCATGTCTGGTTC | | 22 |
| AS29 | ATCTGTGACGAGACCAAGA | | 23 |

NOTES:
[a]Bases from exon 1 are in capital letters and bases from intron 1 in small letters. Vertical bars indicate identity between exogenous (human) and endogenous (mouse) COL1A1 gene. For both exogenous and endogenous genes, the adenine at the start of transcription was counted as position +1.
[b]MS3 (SEQ ID NO: 6) contains the same content in A, C, G and T as AS3 (SEQ ID NO: 5), but in a random order.
[c]S3 (SEQ ID NO: 7) is the sense version of AS3 (SEQ ID NO: 5).
[d]Same sequence as AS3 (SEQ ID NO: 5), except for one mismatch (underlined base).
[e]Same sequence as AS12 (SEQ ID NO: 13), except for one mismatch (underlined base).

None of the oligonucleotides tested were effective in inhibiting expression of either the exogenous or the endogenous gene when the oligonucleotide was administered without any carrier, even at concentrations up to 25 μM. However, several of the oligonucleotides designed as antisense inhibitors of the exogenous gene were effective when administered with 10 μg/ml lipofectin which increases the uptake of nucleic acid, Chiang, M. -Y. et al., *J. Biol. Chem.* 1991, 266, 18162–18171. The oligonucleotide that which was the most effective of the group tested, AS3 (SEQ ID NO: 5), reduced the relative expression of the exogenous gene to about 43% of the control. See FIG. 1 and Table 2. The missense oligonucleotide MS3 (SEQ ID NO: 6) reduced expression to about 81% of the control. The sense oligonucleotide S3 reduced expression to about 74% of the control. However, the small degrees of inhibition seen with MS3 (SEQ ID NO: 6) and S3 were not consistently observed in all experiments. The relative effectiveness of the oligonucleotides was more apparent when the values were compared to the variable values seen with the missense oligonucleotide MS3 (SEQ ID NO: 6). On this basis, AS3 (SEQ ID NO: 5) was the most effective oligonucleotide tested and reduced the expression of the exogenous gene to 53% of the control. Also, as indicated in Table 2, altering a single nucleotide at one site in AS3 (SEQ ID NO: 5) had little effect (see AS7 (SEQ ID NO: 8)). However, a single nucleotide change at another site in AS3 (SEQ ID NO: 5) significantly decreased the effectiveness of the oligonucleotide (see AS16 (SEQ ID NO: 16)).

TABLE 2

EFFECTS OF ANTISENSE OLIGONUCLEOTIDES
AGAINST EXPRESSION OF EXOGENOUS GENE (COL1A1)

| | COL1A1 EXPRESSION[a] | | | RATIOS | |
|---|---|---|---|---|---|
| Oligonucleotide | Endogenous | Exogenous | Exo/Endo | % of Control[b] | % of MS3 Value[b] |
| Control | 10.5 ± 0.2 | 4.4 ± 0.2 | 0.42 ± 0.03 | | 123 |
| AS3 (SEQ ID NO: 5) | 9.0 ± 0.8 | 1.7 ± 0.2 | 0.18 ± 0.01 | 43[d] | 53[d] |
| MS3 (SEQ ID NO: 6) | 10.7 ± 1.4 | 3.6 ± 0.2 | 0.34 ± 0.05 | 81 | |
| S3 (SEQ ID NO: 7) | 11.4 ± 1.7 | 3.5 ± 0.2 | 0.31 ± 0.06 | 74 | 91 |
| AS7[c] (SEQ ID NO: 8) | 11.3 ± 1.3 | 2.5 ± 0.2 | 0.22 ± 0.04 | 52[d] | 65 |
| AS8 (SEQ ID NO: 9) | 8.1 ± 0.3 | 1.5 ± 0.1 | 0.19 ± 0.01 | 45[d] | 54[d] |
| AS9 (SEQ ID NO: 10) | 12.1 ± 1.1 | 3.0 ± 0.2 | 0.25 ± 0.06 | 60[e] | 74 |
| AS10 (SEQ ID NO: 11) | 14.0 ± 2.9 | 4.2 ± 0.7 | 0.31 ± 0.06 | 74 | 91 |
| AS11 (SEQ ID NO: 12) | 10.3 ± 0.9 | 2.4 ± 0.2 | 0.23 ± 0.01 | 55[d] | 68[e] |
| AS16[c] (SEQ ID NO: 16) | 10.1 ± 1.1 | 3.0 ± 0.2 | 0.30 ± 0.01 | 71[d] | 88 |

NOTES:
[a]Expression assayed in arbitrary units by densitometry of Western blots (see FIG. 1). Values are mean ± standard deviation (n = 3).
[b]To correct for variability in cell number among samples, effects were evaluated from the ratio of protein from the exogenous to the endogenous gene versus untreated control or cells treated with missense oligonucleotide MS3 (SEQ ID NO: 6).
[c]Differ by one nucleotide from AS3 (SEQ ID NO: 5) (Table 1).
[d]p value < 0.001.
[e]p value < 0.01.

In additional control experiments, two antisense oligonucleotides (AS12 (SEQ ID NO: 13) and AS15 (SEQ ID NO 15)) were shown to significantly inhibit the relative expression of the endogenous gene (Table 3). In still another control, an antibody to fibronectin was used to assay expression of the fibronectin gene in presence of different oligonucleotides. Insignificant and variable decreases and increases in fibronectin gene expression, observed by Western blot assays, more similar to the variable decreases and increases observed with the same oligonucleotides on expression of the endogenous COL1A1 gene (Table 2).

TABLE 3

EFFECTS OF ANTISENSE OLIGONUCLEOTIDES
AGAINST EXPRESSION OF ENDOGENOUS GENE

| | COL1A1 EXPRESSION | | RATIO | |
|---|---|---|---|---|
| Oligonucleotides | Endogenous | Exogenous | Endo/Exo | % of Control[a] |
| Control | 13.5 ± 2.4 | 6.2 ± 1.3 | 2.18 ± 0.07 | |
| AS12 (SEQ ID NO: 13) | 2.2 ± 0.1 | 1.5 ± 0.4 | 1.46 ± 0.27[c] | 67[d] |
| Control | 15.2 ± 0.8 | 4.2 ± 0.2 | 3.60 ± 0.24 | |
| AS14[b] (SEQ ID NO: 14) | 6.7 ± 1.5 | 2.6 ± 0.2 | 2.48 ± 0.54 | 69 |
| AS15[b] (SEQ ID NO: 15) | 6.1 ± 0.1 | 3.0 ± 0.3 | 2.03 ± 0.16 | 56[c] |

NOTES:
[a]Effects evaluated from the ratios as indicated in Table 2.
[b]Differs by one nucleotide from AS12 (SEQ ID NO: 13) (see Table 1).
[c]p value < 0.001.
[d]p value < 0.01.

Example 6 Inhibition of mRNAs by Antisense Oligonucleotides

Figure 2:
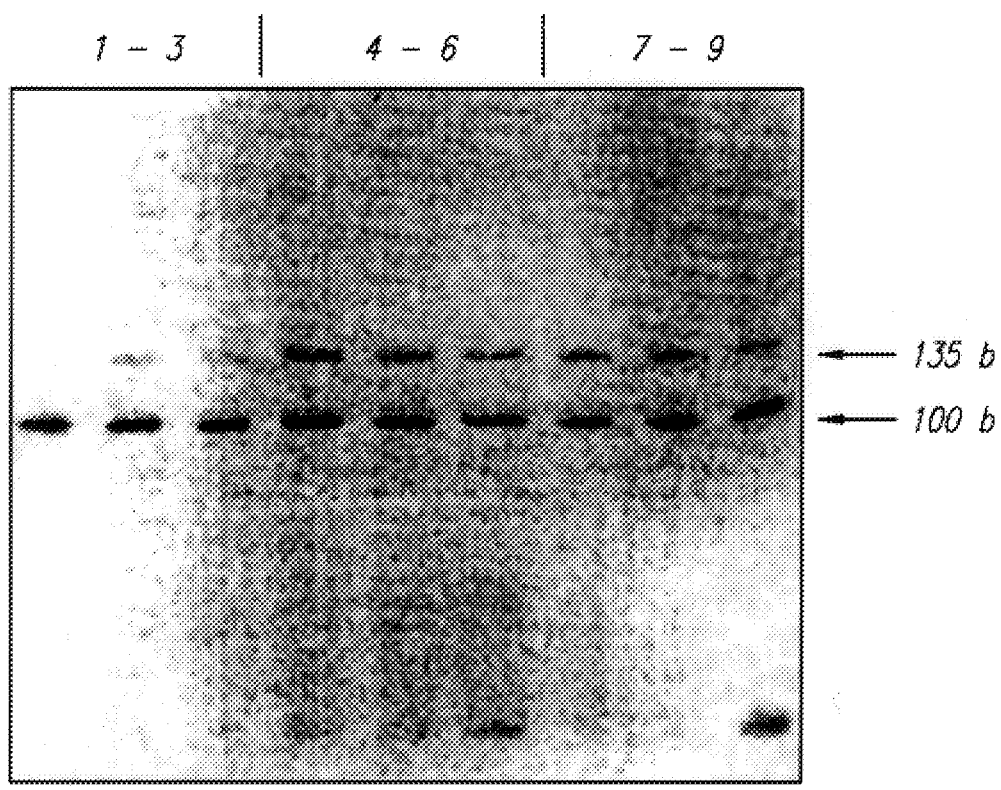
FIG. 2 shows an assay of the steady-state levels of mRNAs from the exogenous (SEQ ID NO: 3) and endogenous (SEQ ID NO: 4) genes. mRNA from the exogenous COL1A1 gene generates a band of 135 bases and mRNA from the endogenous COL1A1 gene generates a band of 100 bases under the conditions of the experiment in which the same oligonucleotide primers are used to synthesize cDNAs from the mRNAs and cDNAs are amplified by the polymerase chain reaction followed by cleavage with a restriction endonuclease (BstNl). Lanes 1–3: Treatment with 0.2 μM AS3 and 10 μg/ml lipofectin. Lanes 4–6: 0.2 μM MS3 and 10 μg/ml lipofectin. Lanes 7–9: 10 μg/ml lipofectin alone. Densitometry of the film demonstrated that AS3 decreased the level of the human mRNA to 80% of the value obtained with MS3 (SEQ ID NO: 6). There was no effect on the level of the mouse mRNA. Three samples of cells were treated identically and analyzed separately in the lanes shown.

To verify the effects of the oligonucleotides, the mRNAs from cells were transcribed into single-stranded cDNAs using an oligonucleotide that primed both the mRNA for the human and mouse proα1 (I) chain. The single-stranded cDNA was then amplified by PCR using a single set of primers with one of the primers labeled with $^{32}$P. The antisense oligonucleotide AS3 (SEQ ID NO: 5) selectively decreased the steady-state level of mRNA for proα1 (I) chains from the exogenous gene to about 50% of the control value (FIG. 2). In the same experiments, the relative expression at the protein level was also decreased by about 50%.

Example 7 Time Course for the Effects of Antisense Oligonucleotide

Figure 3:
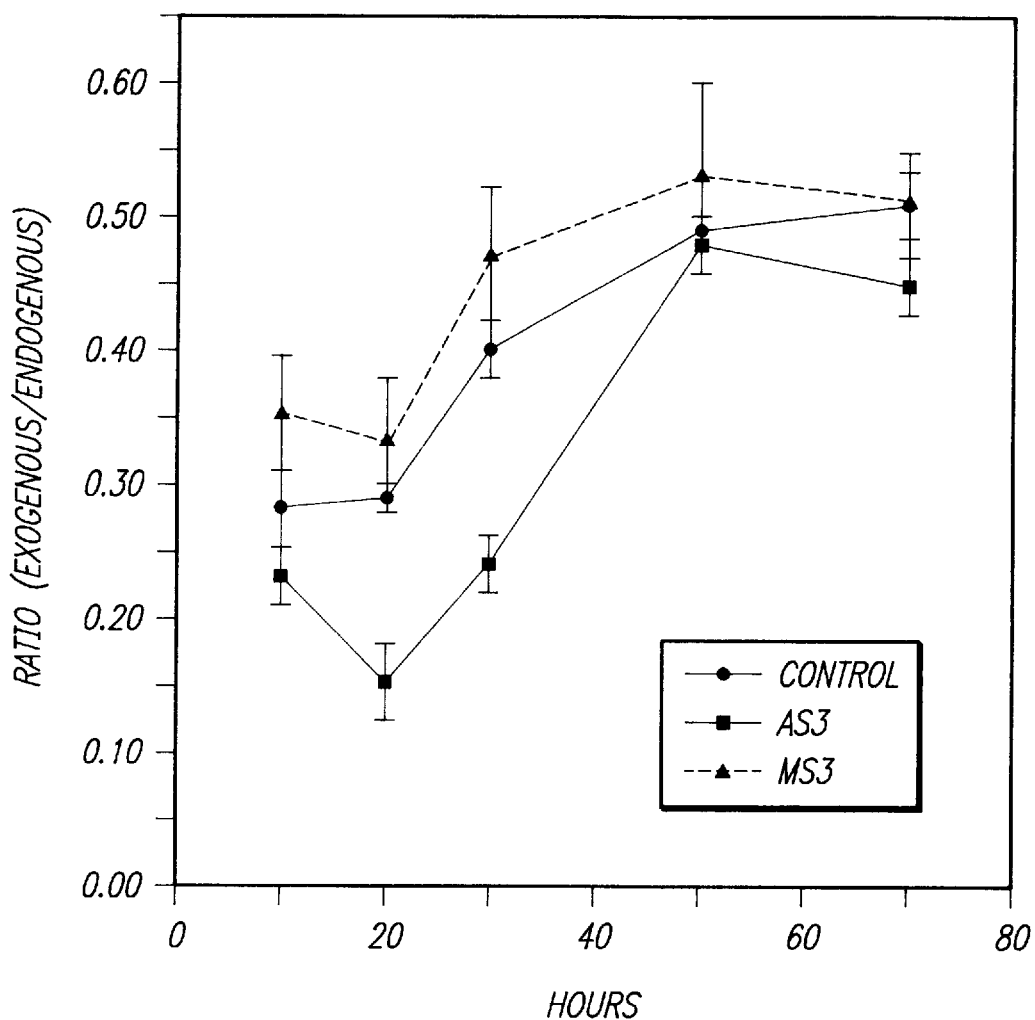
FIG. 3 shows a time course for the specific inhibition of expression of the exogenous COL1A1 gene (SEQ ID NO: 1). Cells were removed at the times indicated and expression of the genes was assayed by Western blotting (see FIG. 1). Values are mean ±(plus/minus) standard deviation (n=3).

After exposure of the cells to the oligonucleotide and lipofectin in serum-free medium for 4 hours, maximal inhibition with AS3 (SEQ ID NO: 5) was observed in about 20 hours (FIG. 3). The inhibition began after 8 hours and persisted for at least 30 hours. Re-exposure of the cells after 24 hours to the oligonucleotide and lipofectin in serum-free medium did not increase the degree of inhibition.

Example 8 Effects of Varying the Concentrations of Lipofectin and Oligonucleotides Optimal inhibition was obtained with 5 μg/ml of lipofectin and 0.1 μM of the oligonucleotide AS3 (SEQ ID NO: 5) (Table 4). With these conditions, expression of the exogenous gene was specifically reduced to 22% of the value seen using the MS3 oligonucleotide (SEQ ID NO: 6). Less inhibition was observed with 5 μg/ml of lipofectin and higher concentrations of oligonucleotide, possibly because saturation of the cationic lipid with oligonucleotide prevented fusion with cell embranes. Chiang, M. -Y. et al., *J. Biol. Chem.* 266: 18162–8171, 1991.

TABLE 4

EFFECTS OF VARYING CONCENTRATIONS OF LIPOFECTIN AND OLIGONUCLEOTIDES AS3 (SEQ ID NO: 5) AND MS3 (SEQ ID NO: 6)

| Lipofectin (μg/ml) | Oligo- nucleotide (μM) | Expression Ratio (Exo/Endo) AS3 (SEQ ID NO: 5) | MS3 (SEQ ID NO: 6) | % of MS3 Value[a] |
|---|---|---|---|---|
| 2.5 | 0 | 0.45 ± 0.05 | | |
| 2.5 | 0.05 | 0.31 ± 0.01 | 0.48 ± 0.00 | 76[c] |
| 2.5 | 0.1 | 0.30 ± 0.00 | 0.41 ± 0.05 | 64 |
| 2.5 | 0.2 | 0.42 ± 0.00 | 0.46 ± 0.05 | 91 |
| 2.5 | 0.4 | 0.49 ± 0.06 | 0.49 ± 0.03 | 100 |
| 5 | 0 | 0.44 ± 0.01 | | |
| 5 | 0.05 | 0.24 ± 0.03 | 0.47 ± 0.01 | 51[d] |
| 5 | 0.1 | 0.11 ± 0.01 | 0.50 ± 0.00 | 22[c] |
| 5 | 0.2 | 0.19 ± 0.05 | 0.39 ± 0.02 | 49 |
| 5 | 0.4 | 0.24 ± 0.05 | 0.44 ± 0.06 | 54 |
| 10 | 0 | 0.46 ± 0.09 | | |
| 10 | 0.05 | 0.35 ± 0.05 | 0.44 ± 0.07 | 79 |
| 10 | 0.1 | 0.30 ± 0.01 | 0.39 ± 0.04 | 77 |
| 10 | 0.2 | 0.14 ± 0.02 | 0.36 ± 0.04 | 39[d] |
| 10 | 0.4 | 0.27 ± 0.02 | 0.62 ± 0.00 | 44[c] |

NOTES:
[a]Effects evaluated from the ratios as indicated in Table 2. All conditions were tested in duplicate.
[c]p value < 0.001.
[d]p value < 0.01.

Example 9 Inhibition of Hepatic Fibrosis in Rats Produced By Carbon Tetrachloride and Dimethylnitrosamine Cirrhosis of the liver is a potentially lethal condition in which normal liver tissue is gradually replaced by collagen fibers following injury to liver by viruses, alcohol or toxic chemicals. The development of hepatic fibrosis is frequently studied experimentally in rats by administering carbon tetrachloride or dimethylnitrosamine to the rats.

A typical series of experiments were reported by L. Ala-Kokko et al., *Hepatology* 1991, 16, 167–172.

In these experiments, female Sprague-Dawley rats, 8 weeks old, were used for the induction of liver fibrosis. The initial body weight of the animals was approximately 200 gm. The animals were maintained on a normal diet with free access to water and a 12-hour light and dark cycle. For induction of hepatic damage with $CCl_4$, the $CCl_4$ was mixed with an equal volume of mineral oil and injected intraperitoneally at doses of 0.1 ml/100 gm body weight, twice a week for 42 days. The animals were killed at regular intervals over a period of 42 days. Five control animals and seven test animals were injected at the same time. For induction of hepatic damage with dimethylnitrosamine (DMN), doses of 1 μl (diluted 1:100 with 0.15 mol/L NaCl) per 100 gm body weight were administered. The injections were made on the first 3 days of each week over a period of 28 days. Treated animals were killed on days 7, 14, 21 or 28. Control animals were killed at the same time. Each group killed on a given day consisted of five control and seven treated animals.

Rats were anesthetized with diethylether and the livers were immediately removed and frozen in liquid nitrogen. The livers were stored frozen at −70° until analyzed. Samples of serum were removed at the same time and stored frozen.

Animals were given humane care and all protocols were reviewed by an institutional review board.

The livers were thawed and homogenized in a teflon and glass homogenizer. A portion of the homogenate was taken for protein measurements. A portion of the homogenate was used for assays of hydroxyproline alter hydrolysis in 6 mol/L HCl and dansyl modification.

Frozen liver specimens of 30–200 mg were homogenized with a Teflon and glass homogenizer (1500 rpm, 50 strokes) in buffer containing 1% (wt/vol) sodium dodecyl sulfate (SDS), 5 mmol/L $Na_2$ EDTA and 10 mmol/L Tris-HCl (pH 7.4). Proteinase K (100 μg/ml) was added to the liver homogenates and cell pellets dissolved in the aforementioned buffer. Samples were then incubated at 40° C. for 1 hour. After incubation the samples were extracted with one vol phenol/chloroform/isoamyl alcohol (25:25:1, vol/vol) followed by 66% (vol/vol) ethanol, 0.2 mol/L NaCl precipitation at −20° C. overnight and centrifugation at 8,000 g for 1 hour at −20° C. The sample was dissolved in 6 mol/L guanidine hydrochloride and the sample was centrifuged at about 2,000 g for 30 minutes. The pellet was re-extracted with 6 mol/L guanidine hydrochloride. The combined supernatants were precipitated by adding a 0.5 vol ethanol. The RNA was further purified by washing the samples with 3 mol/L sodium acetate (pH 6) and alter that with 66% ethanol and 0.1 mol/L NaCl. The RNA samples were then freezedried, dissolved in a buffer containing Tris-HCl and sodium EDTA, frozen in liquid nitrogen and stored at −70° C. until used. RNA content was assayed alter purification by spectrophotometric absorption at 260 nm. The ratio of absorbencies 260 to 280 nm were about 2:1.

The mRNAs were assayed by slot blot hybridization with complementary DNA (cDNA) probes labeled with $^{32}$P by nick translation. Three dilutions of RNA (1–10 μg) were dotted onto nitrocellulose paper with a vacuum manifold (Minifold II; Schleicher and Schuell, Dassel, Germany). The filters were baked, prehybridized and hybridized in the presence of the labeled cDNA probes. The prehybridization and hybridization solutions were 50% formamide, 5× Denhardt's solution, 5× standard saline citrate, 0.1% SDS and 250 μg/ml salmon sperm DNA. The temperature was 42° C.

The filters were washed twice in 1× standard saline citrate and 0.1% SDS at room temperature for 15 minutes and then twice in 0.1× standard saline citrate and 0.1% SDS at 55° C. for 30 minutes. The cDNA probes were for the human proα1(I) chain, the human proα1 (III) chain, the mouse α1(IV) chain, the mouse α2(IV) chain, and the mouse laminin B2 chain.

For histologic evaluation of hepatic fibrosis, thin slices of liver were fixed in 10% neutral-buffered formalin and embedded in paraffin. Sections were cut at 5 μm thickness, stained with hematoxylin and eosin and the Masson trichrome stain for collagen, and subjected to silver impregnation for the demonstration of reticulin fibers. Microscopic evaluation of fibrosis, liver cell damage, inflammation and ductular cell proliferation was performed without knowledge of the source of the specimen. The various parameters were graded from 0 to +3 in order of increasing severity.

As indicated in Table 5, treatment of rats with DMN or $CCl_4$ increased the total content in liver of collagen hydroxyproline. To confirm the fibrotic effects of the two agents, livers from the rats were examined by light microscopy, without knowledge of the source of the specimen. As indicated in Table 6, the expected fibrotic changes were observed. The degree of hepatic fibrosis increased with time in rats treated with both $CCl_4$ and DMN. Histologic evidence of liver cell damage, assessed by cytoplasmic and nuclear pleomorphism, tinctorial properties and hepatic necrosis, tended to increase with time. In further studies, the steady-state levels of mRNAs for type I procollagen, type III procollagen, type IV collagen and the B2 chain of laminin were assayed. As indicated in Table 5, there were marked increases in the levels of mRNAs for α1(I), α1(III) and α1(IV) chains.

The results of these experiments demonstrate increases in the expression of genes for collagen are an integral part of the fibrotic response of liver to injury. Therefore, using antisense oligonucleotides targeted to one or more of the collagen genes would provide an effective method of limiting the fibrotic response. Also, the experiments in rats provide a useful system for testing the effectiveness of the oligonucleotides. For example, administering an oligonucleotide that inhibits expression of the COL1A1 gene for type I procollagen should inhibit the increase in mRNA for the α1(I) chain for type I collagen and the increase in collagen liver hydroxyproline seen in Table 5. Therefore, the oligonucleotide should prevent the fibrosis seen in Table 6. Obtaining such results in rats should provide part of the information necessary to test the effectiveness of the same oligonucleotide for preventing liver fibrosis and cirrhosis and other fibrotic conditions in man and other mammals.

Example 10 Strategy For Developing Haplotype-Specific Antisense Oligonucleotides Mutations in the two genes for type I procollagen cause osteogenesis imperfecta and a subset of osteoporosis, mutations in the gene for type II procollagen cause chondrodysplasias and some forms of osteoarthritis, and mutations in the gene for type III procollagen cause Ehlers-Danlos syndrome type IV and a subset of aneurysms. Also, mutations in the genes for type IV collagen cause the renal disease and other features of the Alport syndrome. Mutations in type IV collagen may also cause glomerulonephrosis and more common renal diseases. Examination of the collagen mutations causing these diseases, however, has demonstrated that most unrelated probands and families have a different mutation in the same collagen gene. Therefore, if an antisense oligonucleotide were designed to target the specific base change that causes a disease in a family, a custom-made test would have to be made for each family. However, the presence of neutral sequence variations in many collagen genes makes it possible to design a relatively small panel of oligonucleotides that can be used for many different mutations in different families. As indicated in Table 7, 25 neutral sequence variations have now been identified in the human gene for type II procollagen. The sequence variations occur both in introns and exons of the gene. Similar neutral sequence variations have been seen in most other genes examined. In the case of the cluster of human β-globin genes, neutral sequence variations in the large cluster of genes have been used to define specific haplotypes of the gene, i.e., patterns of neutral variations in and around the genes that can be used to distinguish the gene cluster of one chromosome from another.

Orkin, S., *The Molecular Basis of Blood Diseases,* G. Stamatoyannopoulos, A. W. Nieehuis, P. Leder and P. W. Majerus, Eds., W. B. Saunders, Philadelphia, 1987, p 166. It is very likely that the neutral sequence variants seen in human type II procollagen gene define specific neutral haplotypes of the gene. For example, the 25 neutral variations shown in Table 7 probably occur within specific patterns in alleles of the gene so that they define many fewer than 25 different alleles. The presence of such neutral variations provides specific target sites for oligonucleotides to inhibit expression of specific alleles of type II procollagen gene. Therefore, if a disease in a proband or family is shown to be caused by the mutation in a specific allele, an oligonucleotide targeted to a neutral sequence variation in the same allele will be effective in inhibiting expression of the allele. Therefore, if the 25 neutral variations shown in Table 7 define five specific alleles of collagen II gene, five specific oligonucleotides will be adequate to specifically inhibit expression of a large number of different mutations that may occur in the same allele.

TABLE 5

EFFECTS OF $CCl_4$ AND DMN ON LIVER CONTENT OF COLLAGEN HYDROXYPROLINE AND STEADY-STATE LEVELS OF mRNAs

| | Liver | Steady-state levels of mRNAs | | | | |
|---|---|---|---|---|---|---|
| Days | hydroxyproline | a(I) | a1(III) | a1(IV) | a2(IV) | B% |
| $CCl_4$ | | | | | | |
| 7 | 115 ± 24 | 142 ± 75 | 198 ± 89 | 147 ± 46 | 125 ± 24 | 149 ± 54 |
| 14 | 155 ± 45 | 268 ± 94 | 143 ± 77 | 270 ± 72 | 127 ± 52 | 231 ± 58 |
| 21 | 132 ± 37 | 248 ± 91 | 302 ± 38 | 180 ± 52 | 145 ± 34 | 138 ± 42 |
| 28 | 225 ± 139 | 376 ± 200 | 422 ± 225 | 193 ± 65 | 98 ± 4 | 79 ± 25 |
| 42 | 196 ± 35 | 288 ± 197 | 343 ± 123 | 272 ± 78 | 125 ± 24 | 115 ± 8 |
| DMN | | | | | | |
| 7 | 156 ± 95 | 180 ± 79 | 105 ± 23 | 233 ± 72 | 142 ± 45 | 169 ± 47 |

TABLE 5-continued

EFFECTS OF $CCl_4$ AND DMN ON LIVER CONTENT OF COLLAGEN HYDROXYPROLINE AND STEADY-STATE LEVELS OF mRNAs

| Days | Liver hydroxyproline | Steady-state levels of mRNAs | | | | |
|---|---|---|---|---|---|---|
| | | a(I) | a1(III) | a1(IV) | a2(IV) | B% |
| 14 | 165 ± 37 | 158 ± 71 | 146 ± 55 | 171 ± 63 | 118 ± 32 | 278 ± 53 |
| 21 | 237 ± 112 | 436 ± 273 | 315 ± 60 | 214 ± 67 | 399 ± 68 | 373 ± 143 |
| 28 | 236 ± 83 | 1,438 ± 386 | 460 ± 51 | 451 ± 171 | 153 ± 42 | 253 ± 86 |

Values are mean relative to controls ± S.D. Values for liver hydroxyproline were first calculated as milligrams of hydroxyproline per gram wet weight of liver and then as percent of control values. Arbitrary absorbance units obtained by densitometric scanning of slot blots. Control values were adjusted to 100%.

TABLE 6

HISTOLOGICAL FINDINGS OF LIVERS OF RATS

| Days | Liver cell damage | Presence of ductules | Inflammation | | Fibrosis |
|---|---|---|---|---|---|
| | | | Portal | Parenchymal | |
| $CCl_4$ | | | | | |
| 7 | 1.1 ± 0.36 | 0 | 0.3 ± 0.49 | 0.3 ± 0.49 | 0 |
| 14 | 2.9 ± 0.38 | 0.9 ± 0.38 | 1.0 ± 0.58 | 1.3 ± 0.95 | 0.3 ± 0.39 |
| 21 | 2.3 ± 0.49 | 1.1 ± 1.1 | 1.4 ± 0.98 | 1.7 ± 1.38 | 1.2 ± 0.39 |
| 28 | 1.3 ± 0.82 | 0.8 ± 0.70 | 0.9 ± 0.69 | 0.7 ± 0.76 | 1.0 ± 0.65 |
| 42 | 2.7 ± 0.49 | 0.9 ± 0.38 | 0.9 ± 0.78 | 0.7 ± 0.76 | 2.1 ± 0.19 |
| DMN | | | | | |
| 7 | 2.1 ± 0.69 | 0.3 ± 0.49 | 1.3 ± 0.98 | 0.9 ± 0.69 | 0.6 ± 0.53 |
| 14 | 2.4 ± 0.53 | 0.6 ± 0.53 | 0.9 ± 0.38 | 0 | 0.4 ± 0.53 |
| 21 | 2.1 ± 0.69 | 0.6 ± 0.53 | 0.9 ± 0.69 | 0.3 ± 0.49 | 1.0 ± 0 |
| 28 | 3.0 ± 0 | 1.6 ± 0.53 | 1.1 ± 0.38 | 2.0 ± 1.0 | 1.2 ± 0.57 |

Histological findings graded on scale of 0 to +3, with control being 0. Values refer to the mean and standard deviations of seven rats in each treatment group.

TABLE 7

TYPE II PROCOLLAGEN NEUTRAL SEQUENCE VARIANTS

| REGION | NUCLEOTIDE[a] | | ALLELES | | OBSERVED FREQUENCY | VERIFICATION |
|---|---|---|---|---|---|---|
| | POSITION | TYPE | MAJOR | MINOR | | |
| Exon 5B* | 75 ($Gly_{-50}$) | base substitution | C | A | 0.25 | R.E. |
| Intron 9 | +15 | base substitution | G | A | 0.48 | R.E. |
| Intron 9* | +42 | base deletion | G | | 0.16 | R.E. |
| Exon 19* | 21 ($Gly_{229}$) | base substitution | T | C | 0.02 | R.E. |
| Exon 24* | 3 ($Gly_{361}$) | base substitution | T | G | 0.01 | R.E. |
| Exon 26 | 3 ($Gly_{412}$) | base substitution | T | C | 0.1 | PCR-I R.E. |
| Intron 26 | −24 | base substitution | C | A | 0.1 | R.E. |
| Intron 26* | −47 | base substitution | C | T | 0.4 | PCR-I R.E. |
| Exon 30* | 30 ($Gly_{493}$) | base substitution | C | T | 0.03 | RSS |
| Intron 30* | +7 | base substitution | A | C | 0.1 | RSS |
| Intron 30* | +37 | base substitution | G | T | 0.1 | RSS |
| Intron 31* | +7 | base substitution | G | A | 0.03 | RSS |
| Intron 31* | +56 | base substitution | C | T | 0.1 | R.E. |
| Intron 31* | +101 | base substitution | G | T/A | nd | RSS |
| Intron 31* | +129 | base deletion | G | | nd | RSS |
| Intron 31* | −55 | base substitution | T | G | 0.4 | RSS |
| Intron 31* | −54 | base deletion | G | | 0.4 | RSS |
| Intron 31* | −49 | base substitution | C | T | 0.4 | RSS |
| Exon 32 | 102 ($Gly_{565}$) | base substitution | T | C | 0.35 | R.E. |
| Intron 32 | −22 | base substitution | G | A | 0.4 | R.E. |
| Intron 32* | −32 | base substitution | T | C | 0.4 | R.E. | nd = not determined;
RSS = reverse strand sequencing;
R.E. = restriction enzyme analysis;
PCR-I R.E. = PCR-introduced restriction enzyme site analysis
[a]Position for exon is designated without a ± sign.
Position in intron is designated with a "−" sign if the sequence variant is located 5' to the next exon and with a "+" sign if the sequence variant is located 3' to the preceding exon.
*Sequence variants which are new to this report

What is claimed:

1. An oligonucleotide consisting of 10 to 50 nucleotides having a nucleotide sequence that stably hybridizes in a cell in culture to the exon 1/intron 1 boundary of a mutant or normal wild type COL1A1 gene encoding proα1(I) chain of type I procollagen, wherein said oligonucleotide inhibits expression of said mutant or normal wild type COL1A1 gene.

2. The oligonucleotide of claim 1 of SEQ ID NO: 18.

3. The oligonucleotide of claim 1 in a pharmaceutically acceptable carrier or diluent.

4. An oligonucleotide consisting of a sequence selected from the group consisting of SEQ ID NO:5, SEQ ID NO:8, SEQ ID NO:9, SEQ ID NO: 10, SEQ ID NO:11, SEQ ID NO: 12, SEQ ID NO: 13, SEQ ID NO:14, SEQ ID NO:15, SEQ ID NO:16, SEQ ID NO:19, SEQ ID NO:20, SEQ ID NO:21, SEQ ID NO:22 and SEQ ID NO:23.

5. A method of inhibiting mutant collagen gene expression in a cell in culture which comprises contacting a cell containing a mutant COL1A1 gene with an inhibitory amount of an oligonucleotide consisting of 10 to 50 nucleotides having a nucleotide sequence that stably hybridizes to the exon 1/intron 1 boundary of said mutant COL1A1 gene.

6. The method of claim 5 wherein said oligonucleotide consists of SEQ ID NO: 18.

7. A method of inhibiting normal collagen gene expression in cell culture which comprises contacting a cell containing a normal COL1A1 gene with an inhibitory amount of an oligonucleotide consisting of 10 to 50 nucleotides having a nucleotide sequence that stably hybridizes to the exon 1/intron 1 boundary of said normal COL1A1 gene.

\* \* \* \* \*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i v ) ANTI-SENSE: NO ( x i ) SEQUENCE DESCRIPTION: SEQ ID NO:1:

TTGGCCCTGT CTGCCT        16

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i v ) ANTI-SENSE: NO ( x i ) SEQUENCE DESCRIPTION: SEQ ID NO:2:

TGAATGCAAA GGAAAAAAAT        20

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:3:

CAAGTCGAGG GCCAAGACGA AGACAGT        27

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:4:

CTCCTGACGC ATGGCCAAGA AGACAGT        27

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:5:

ACTGTCTTCG TCTTGGCCCT                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:6:

ATCCTGCTTC GTTCTGGCTC                    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:7:

AGGGCCAAGA CGAAGACAGT                    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:8:

ACTGTATTCG TCTTGGCCCT                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:9:

TGTCTTCGTC TTGGCCCTCG                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:10:

TCTTCGTCTT GGCCCTCGAC                    20

(2) INFORMATION FOR SEQ ID NO:11:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i v ) ANTI-SENSE: YES ( x i ) SEQUENCE DESCRIPTION: SEQ ID NO:11:

ACTGTCTTCG TCTTG                                                                        15

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:12:

GTCTTGGCCC TCGACTTG                                                                     18

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:13:

ACTGTCTTCT TGGCCATGCG                                                                   20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:14:

ACTGTATTCT TGGCCATGCG                                                                   20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:15:

ACTGTCTACT TGGCCATGCG                                                                   20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:16:

ACTGTCTACG TCTTGGCCCT                                    20

( 2 ) INFORMATION FOR SEQ ID NO:17:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:17:

ACTAAGTTTG A                                             11

( 2 ) INFORMATION FOR SEQ ID NO:18:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:18:

NMNWCGNCNN G                                             11

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:19:

ATCCGCGCCG AGGGCAACA                                     19

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:20:

GTACCATGAC CGAGACGTGT                                    20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:21:

GCTTCGACGT TGGCCCTGTC                                            20

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:22:

ACAAGAGGCA TGTCTGGTTC                                            20

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:23:

ATCTGTGACG AGACCAAGA                                             19